United States Patent
Krutmann et al.

(10) Patent No.: US 10,857,089 B2
(45) Date of Patent: *Dec. 8, 2020

(54) COSMETIC COMPOSITIONS COMPRISING PURPLE CONEFLOWER PRESSED JUICE

(71) Applicant: Symrise AG, Holzminden (DE)

(72) Inventors: Jean Krutmann, Düsseldorf (DE); Imke Meyer, Bodenwerder (DE); William Johncock, Reinbek (DE); Gerhard Schmaus, Höxter (DE); Marielle le Maire, Boulogne Billancourt (FR); Martina Herrmann, Hameln (DE)

(73) Assignee: Symrise AG, Holzminden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/577,525

(22) PCT Filed: May 25, 2016

(86) PCT No.: PCT/EP2016/061825
§ 371 (c)(1),
(2) Date: Nov. 28, 2017

(87) PCT Pub. No.: WO2016/189046
PCT Pub. Date: Dec. 1, 2016

(65) Prior Publication Data
US 2018/0360733 A1 Dec. 20, 2018

(30) Foreign Application Priority Data
May 28, 2015 (EP) ..................... 15169751

(51) Int. Cl.
*A61K 8/9783* (2017.01)
*A61Q 17/00* (2006.01)
*A61K 8/35* (2006.01)
*A61K 8/49* (2006.01)
*A61K 8/9794* (2017.01)
*A61K 8/9789* (2017.01)
*A61Q 17/04* (2006.01)
*A61K 36/28* (2006.01)
*A61K 36/9068* (2006.01)
*A61Q 5/00* (2006.01)
*A61K 8/97* (2017.01)

(52) U.S. Cl.
CPC ............. *A61K 8/9783* (2017.08); *A61K 8/35* (2013.01); *A61K 8/4973* (2013.01); *A61K 8/97* (2013.01); *A61K 8/9789* (2017.08); *A61K 8/9794* (2017.08); *A61K 36/28* (2013.01); *A61K 36/9068* (2013.01); *A61Q 5/00* (2013.01); *A61Q 17/00* (2013.01); *A61Q 17/04* (2013.01)

(58) Field of Classification Search
None
See application file for complete search history.

(56) References Cited

U.S. PATENT DOCUMENTS

| 8,241,681 B2* | 8/2012 | Herrmann | A61K 8/34 424/756 |
| 2008/0213202 A1* | 9/2008 | Maes | A61K 8/361 424/59 |
| 2013/0064905 A1* | 3/2013 | Duggan | A61K 38/06 424/725 |
| 2013/0251730 A1 | 9/2013 | Ley et al. | |
| 2014/0242020 A1 | 8/2014 | Meyer et al. | |

FOREIGN PATENT DOCUMENTS

| EP | 2165697 A1 * | 3/2010 | ............. A61K 8/416 |
| FR | 2811573 A1 | 1/2002 | |
| WO | 9620704 A1 | 7/1996 | |
| WO | 0230385 A2 | 4/2002 | |
| WO | 2007003307 A1 | 1/2007 | |
| WO | 2007128723 A1 | 11/2007 | |
| WO | 2007128725 A1 | 11/2007 | |
| WO | 2013055315 A1 | 4/2013 | |

OTHER PUBLICATIONS

Drakaki et al. Frontiers in Environmental Science 2014 2(11):1-6 (Year: 2014).*
Romieu et al. Proceedings of the American Thoracic Society 2010 7:116-122 (Year: 2010).*
Bind et al. Epigenetics 2014 9(3):448-458 (Year: 2014).*
Vimalanathan et al. Pharmaceutical Biology 2009 47(5):430-435). (Year: 2009).*
Davis et al. Journal of Clinical and Aesthetic Dermatology 2010 3(7):20-31 (Year: 2010).*
Choi et al. Journal of Dermatological Science 2012 66:207-215 (Year: 2012).*
Nievergelt et al. Journal of Immunology 2011 187:4140-4150 (Year: 2011).*
Scorza et al. Comparison of Ginger Extracts from Africa and Asia. Juliani et al. ed.; African Natural Plant Products: New Discoveries and Challenges in Chemistry and Quality ACS Symposium Series; American Chemical Society: Washington, DC, 2010 527-535 (Year: 2010).*

(Continued)

*Primary Examiner* — Robert A Wax
*Assistant Examiner* — Caralynne E Helm
(74) *Attorney, Agent, or Firm* — Dilworth & Barrese, LLP

(57) ABSTRACT

Suggested is a cosmetic composition comprising an anti-pollution agent selected from the group consisting of purple coneflower pressed juice, sclareolide, ginger root C02 extract, E/Z-2-benzylindene-5,6-dimethoxy-3,3-dimethylindan-1-one or mixtures thereof, in a working amount sufficient for (a) reducing or preventing air pollution induced gene expression, and/or (b) reducing or preventing a gene expression induced or inducible by polycyclic aromatic hydrocarbons, and/or (c) reducing or preventing air pollution-induced or air pollution-inducible skin damage.

5 Claims, No Drawings

Specification includes a Sequence Listing.

(56) References Cited

OTHER PUBLICATIONS

"SymHelios 1031," Mar. 16, 2011, XP055226140, retrieved from Internet Nov. 5, 2015.

* cited by examiner

COSMETIC COMPOSITIONS COMPRISING PURPLE CONEFLOWER PRESSED JUICE

FIELD OF INVENTION

The present invention belongs to the area of cosmetics and refers to a composition comprising specific agents effective in preventing and curing human skin and hair from diseases induced by air pollution.

STATE OF THE ART

The human skin is the outer covering of the body. In humans, it is the largest organ of the integumentary system. The skin has multiple layers of ectodermal tissue and guards the underlying muscles, bones, ligaments and internal organs. Human skin is similar to that of most other mammals, except that it is not protected by a fur. Though nearly all human skin is covered with hair follicles, it can appear hairless. A wrinkle, also known as a rhytide, is a fold, ridge or crease in the skin. Skin wrinkles typically appear as a result of aging processes such as glycation, habitual sleeping positions loss of body mass, or temporarily, as the result of prolonged immersion in water. Age wrinkling in the skin is promoted by habitual facial expressions, aging, sun damage, smoking, poor hydration, and various other factors. Much work has been done for identifying factors that can inhibit or at least slow down skin ageing. In fact, cosmetic market shows a magnitude of different products often advertised as anti-ageing or anti-wrinkle actives.

On the other side, little attempt has been made with regard to another important factor that lead to skin ageing, formation of wrinkles and may also cause inflammations and perhaps skin cancer: air pollution.

The term air pollution includes but is not limited to the exhausts of traffic, not to forget the exhaust of industry in this context. Air pollution is meaning the released gas pollutants but also the released particles in this context. But also the particles by abrasion of rubber wheels are included. The particles which are involved in air pollution might have bound polycyclic aromatic hydrocarbons (PAH) but are not limited to these PAH rich ones. Also carbon black particles released by printers are an air pollution problem which is occurring indoor. Another problem is the generation of air pollution by indoor cooking with coal or firewood.

The exposure of human skin to repeated air pollution was shown in epidemiological studies to support extrinsic skin aging associated with pigment spots and wrinkles [Vierkoetter et al., J Invest Dermatol 130 (12), 2719-26, 2010]. The formation of pigment spots is due to a crosstalk of keratinocytes and melanocytes, the melanin producing cells of the skin. Keratinocytes release inter alia POMC (proopiomelanocortin) which stimulates melanogenesis in melanocytes. By inhibiting the induction of POMC gene the skin cells are protected against excessive melanin formation. Increased formation of wrinkles is due to an enhanced activity of MMP1 (matrixmetalloproteinase-1) in the skin, an enzyme which is responsible for the degradation of collagen. By inhibiting the induction of MMP1 gene the skin cells are protected against wrinkle formation. Different cytokines like e.g. IL-6 (interleukin-6) results in inflammation but also via post-inflammatory hyperpigmentation into age spots. By inhibiting the induction of IL-6 gene the skin cells are protected against inflammation as well as pigment spot formation.

The aryl hydrocarbon receptor (AhR) (NCBI gene accession number BC0700800) has a central role in the detoxification of exogenous contaminants. It mediates the biological response to polycyclic aromatic hydrocarbons (PAHs) such as benz[a]pyrene and halogenated PAHs such as 2,3,7,8-tetrachlorodibenzo-p-dioxin (TCDD). The AhR is a ligand-activated transcription factor which, after binding a ligand, translocates into the cell nucleus, where it forms a dimer with another transcription factor, namely the aryl hydrocarbon receptor nuclear translocator (ARNT), binds to regulatory gene sequences and induces the transcription of various genes, e.g. CYP1A1 and CYP1 B1. The consequences of AhR activation are the development of skin tumours (Shimizu et al. (2000) 97, 779), irritations and inflammations, the development of allergies, atopic dermatitis and itching, and a perturbation of skin integrity (Tauchi et al. (2005) Mol. Cell Biol. 25, 9360-8; Henley at al., Arch. Biochem. Biophys. (2004) 422, 42-51), as well as the induction of MMP-1 (collagenase-1) (Murphy et al. (2004) J. Biol. Chem. 279, 25284-2593).

UVB light induces CYP1A1 expression in human keratinocytes and lymphocytes and in the mouse hepatoma cell line Hepa-1 (Wei et al., Chem. Biol. Interact. (1999) 118, 127-40). However, it has only been demonstrated for Hepa-1 cells that CYP1A1 induction is AhR-dependent, but, as explained below, AhR activation is dependent on the cell type, so it is not possible to extrapolate from the action on mouse hepatoma cells to the action on human skin cells. Moreover, CYP1A1 can also be induced by AhR-independent pathways (Guigal et al. (2001) Life Sci. 68(18), 2141-50; Tijet et al. (2006) Mol. Pharmacol. 69(1), 140-153). Therefore, there is not necessarily a connection between UVB, the AhR and CYP1A1 in keratinocytes.

While certain mechanisms how air pollution interacts with human skin and hair and creates disorders and dysfunctions, little is known about actives that can prevent and cure damaged human skin and hair. Therefore, the object of the present invention has been to identify suitable actives and active mixtures useful to simultaneously fight the negative consequences that air pollutants provide to human skin and hair, in particular to inhibit the induction of POMC gene, and therefore protects skin cells against excessive melanin formation. Another focus in the fight against the negative consequences that air pollutants provide to human skin and hair, was to provide actives and active mixtures which especially inhibit the induction of MMP1 (matrixmetalloproteinase-1) in the skin to protect the skin against increased formation of wrinkles. A further object was to provide actives and active mixtures which especially inhibit the induction of IL-6 (interleukin-6) to protect skin cells against inflammation as well as pigment spot formation. At last, it was an object to provide actives and active mixtures which inhibit the activation of the AhR (aryl hydrocarbon receptor) measured as induction of the CYP1A1 (Cytochrome P450, Family 1, Subfamily A, Polypeptide 1) gene upregulation, particularly particle induced CYP1A1 gene expression and thus avoiding diseases associated with particle induced AhR activation, particularly airborne particles from air pollution.

DESCRIPTION OF THE INVENTION

Object of the present invention is a cosmetic composition comprising an anti-pollution agent selected from the group consisting of purple coneflower pressed juice, sclareolide, ginger root CO2 extract, E/Z-2-benzylindene-5,6-dimethoxy-3,3-dimethylindan-1-one, or mixtures thereof, preferably purple coneflower pressed juice in a working amount sufficient for (a) reducing or preventing air pollution induced gene expression, and/or
(b) reducing or preventing a gene expression induced or inducible by polycyclic aromatic hydrocarbons, and/or
(c) reducing or preventing air pollution-induced or air pollution-inducible skin damage, especially skin cancer, skin ageing, skin inflammation and hyperpigmentation.

Surprisingly, it has been observed that
purple coneflower pressed juice and/or
sclareolide and/or
ginger root CO2 extract and/or
E/Z-2-benzylindene-5,6-dimethoxy-3,3-dimethylindan-1-one,
taken alone, preferably in binary or ternary mixture, inhibit in vitro on human epidermal keratinocytes the up-regulation of genes involved in skin aging after incubation with model particles described as appropriate surrogates for the study of authentic street particles (Danielsen et al, *Particle and Fibre Toxicology* 2008, 5:6). But also after incubation with indoor particles which have a lower amount of PAHs bound to the particles gene expression was induced. Particularly, purple coneflower pressed juice was capable to inhibit also this up-regulation.

Preferably the cosmetic composition of the present invention comprises as anti-pollution agent purple coneflower pressed juice in a working amount sufficient for
(a) reducing or preventing air pollution induced gene expression, and/or
(b) reducing or preventing a gene expression induced or inducible by polycyclic aromatic hydrocarbons, and/or
(c) reducing or preventing air pollution-induced or air pollution-inducible skin damage, especially skin cancer, skin ageing, skin inflammation and hyperpigmentation.

Binary and Ternary Mixtures

In a preferred embodiment a cosmetic composition of the present invention comprises a binary mixture of said agents, wherein the binary mixture is in particular selected from one of the following binary mixtures:
(i) purple coneflower pressed juice and sclareolide,
(ii) purple coneflower pressed juice and ginger root CO2 extract,
(iii) purple coneflower pressed juice and E/Z-2-benzylindene-5,6-dimethoxy-3,3-dimethylindan-1-one.

The said binary mixtures are particularly advantageously suitable as drugs or non-drugs (especially in cosmetic form) for protecting skin and/or hair, particularly in aspect to the aforementioned effects (a) to (c).

Therefore, a further aspect of the present invention is directed to the preferred binary mixtures themselves as listed above.

In a binary mixture of purple coneflower pressed juice and E/Z-2-benzylindene-5,6-dimethoxy-3,3-dimethylindan-1-one, purple coneflower pressed juice is preferably present in an amount from 10% by weight to 70% by weight, wherein E/Z-2-benzylindene-5,6-dimethoxy-3,3-dimethylindan-1-one is preferably present in an amount from 30% by weight to 90% by weight, with the provision that both substances add together to 100% by weight (mixture III). In another binary mixture of purple cone flower pressed juice and ginger root CO2 extract (mixture ii) or sclareolide (mixture i), the amount of each of those actives is preferably from 20% by weight to 80% by weight, in the composition, with the provision that all actives add together to 100% by weight.

Most preferred is the binary mixture comprising purple coneflower pressed juice and ginger root CO2 extract or sclareolide, wherein ginger root CO2 extract or sclareolide is present in the end product, which is preferably a cosmetic or pharmaceutical product, in an amount from 0.05% by weight to 0.2% by weight, more preferably 0.1% by weight to 0.2% by weight and purple coneflower pressed juice is present in the end product in an amount from 0.01% by weight to 2.0% by weight, more preferably from 0.05% by weight to 0.1% by weight.

In another preferred embodiment the compositions comprise ternary mixtures of said agents, such as
(i) purple coneflower pressed juice, sclareolide and ginger root CO2 extract, or
(ii) purple coneflower pressed juice, sclareolide, and E/Z-2-benzylindene-5,6-dimethoxy-3,3-dimethylindan-1-one; or
(iii) purple coneflower pressed juice, E/Z-2-benzylindene-5,6-dimethoxy-3,3-dimethylindan-1-one and ginger root CO2 extract.

The said ternary mixtures are particularly advantageously to affect additive and/or synergistically effects on the properties of the mixtures for protecting skin and/or hair, particularly in aspect to the aforementioned effects (a) to (c).

Therefore, a further aspect of the present invention is directed to the preferred ternary mixtures (i) to (iii) themselves as listed above.

Preferably purple coneflower pressed juice is present in an amount from 12.5% by weight to 75% by weight, wherein sclareolide is present in an amount from 12.5% by weight to 75% by weight, and ginger root CO2 extract is preferably present in an amount from 12.5% by weight to 75% by weight in a ternary mixture (i), with the provision that all three compounds add together to 100% by weight.

Preferably purple coneflower pressed juice is present in an amount from 5% by weight to 60% by weight, wherein sclareolide is present in an amount from 5% by weight to 60% by weight and E/Z-2-benzylindene-5,6-dimethoxy-3,3-dimethylindan-1-one is preferably present in an amount from 20% by weight to 90% by weight in a ternary mixture (ii), with the provision that all three compounds add together to 100% by weight.

Preferably purple coneflower pressed juice is present in an amount from 5% by weight to 60% by weight, wherein E/Z-2-benzylindene-5,6-dimethoxy-3,3-dimethylindan-1-one is preferably present in an amount from 20% by weight to 90% by weight, and ginger root CO2 extract is preferably present in an amount from 5% by weight to 60% by weight in a ternary mixture (ii), with the provision that all three compounds add together to 100% by weight.

A working amount of an anti-pollution agent, respectively a binary or ternary mixture thereof, means an amount from 0.01% by weight to 2.5% by weight, preferably from about 0.05% by weight to 1.0% by weight of said anti-pollution agent(s), in case of the binary or ternary mixture, the sum of all anti-pollution agents in the mixture—calculated on the final composition.

Purple Coneflower Pressed Juice

Purple coneflower is a common name of the flowering plant *Echinacea purpurea* in the family Asteraceae:

*Echinacea purpurea* is native to eastern North America. *Echinacea* was one of the basic antimicrobial herbs of eclectic medicine from the mid-19th century through the early 20th century, and its use was documented for snakebite, anthrax, and for relief of pain. In the 1930s *echinacea* became popular in both Europe and America as an herbal medicine. Primary use of *Echinacea* preparations today is for prevention and treatment of upper respiratory infections (cold and flu). The valuable constituents of purple coneflower pressed juice are caffeic acid derivatives (mainly cichoric and caftaric aci), polysaccharides, minerals, organic acids, proteins and amino acids. The product is obtainable under the trademark SymFinity® 1298 from Symrise AG, Holzminden (DE).

Ginger Root CO2 Extract

Ginger root extracts with a high content of pungent components are well-known for the flavouring of food and beverages. The characterization of ginger root extracts by HPLC, GC and other analytical methods is well-described. The quantification of pungent components like gingerols, shogaols and zingerone is good laboratory practice. But ginger extracts characterized by a high content of pungent components of 42-50% b.w. have not been described for cosmetic applications before.

The water and/or ethanol and/or water/ethanol extracts of ginger root of unknown composition are described as anti-oxidants and anti-aging agents and are often disclosed as the preferred extracts for these applications. The use of these extracts is described inter alia in JP 2009 073777 A1 for the improvement of wrinkles, in JP 2000 319189 A1 as elastase inhibitors, by Fujimura et al. (Fragrance Journal (2002), 30(6), 38-42) for wrinkle improvement by inhibition of elastase activity. In JP 2007008847 the claimed extract was prepared with 20% ethanol resulting in the concentration of fructosyl dipeptides as active principles.

For the application to hair and scalp ginger tincture, ginger juice and the above mentioned water and/or ethanol and/or water/ethanol extracts of ginger root are well-known. As activities for these extracts on hair and scalp inter alia enhanced microcirculation is described. For example, CN 102451128 A1 suggests a shampoo claimed to prevent hair loss contains 5% ginger juice. JP 63 091315 A1 describes microcirculation enhancing ginger juice in shampoo formations for hair growth stimulation. EP 1281402 B1 (Kao) refers to a ginger extract substantially free of gingerols for hair growth inhibition.

Ginger oil was used as a soothing, relaxing or warming agent in cosmetic formulations in WO 2009 087578 A1 (Foamix). But the document did not disclose the composition of the ginger oil. The essential oil of ginger is known for a strong pungent smell and taste due to the volatile constituents and is not comparable to the ginger pungent extract according to the present invention.

The isolation of the pungent components of ginger is described in different documents. Ficker et al. (Phytotherapy Research (2003), 17(8), 897-902) evaluated the anti-fungal activity of ginger constituents.

The evaluation of anti-inflammatory activity of pungent components of ginger was given in different documents, inter alia by Lantz et al. (Phytomedicine (2007), 14(2-3), 123-128). Additionally the anti-tumour activity and proliferation inhibitory activity on tumour cells were evaluated by different groups, inter alia by Sang et al. (Journal of Agricultural and Food Chemistry (2009), 57(22), 10645-10650).

In CN 1840162 A1 a ginger root $CO_2$ extract is described without specifying the content of pungent components like gingerols and shogaols. The extract is disclosed as an anti-inflammatory extract. Application examples are tablets, pills and capsules for oral consumption. Examples for topical application on skin are not described.

Ginger root CO2 extracts that are particularly preferred in the content of the present invention contain
(a) 25 to 30% b.w. [6]-gingerol
(b) 5 to 10% b.w. [8]-gingerol
(c) 5 to 10% b.w. [10]-gingerol
(d) 1.5 to 4% b.w. [6]-shogaol
(e) 0.3 to 1.3% b.w. [8]-shogaol;
(f) 0.03 to 1 b.w. [10]-shogaol;
(g) 0.01 to 1 b.w. zingerone, on condition that the amount of gingerols sums up to 35 to 50% b.w. and the amount of shogaols sums up to 1.5 t 6% b.w. Extracts of this kind are subject to EP 2772245 A1 (SYMRISE) which is hereby incorporated by reference with regard to the nature of the extracts and the manner how to obtain them. The product is obtainable under the trademark SymVital® AgeRepair 3040 from Symrise AG, Holzminden (DE).

E/Z-2-Benzylindene-5,6-Dimethoxy-3,3-Dimethyl-indan-1-One

E/Z-2-benzylindene-5,6-dimethoxy-3,3-dimethylindan-1-one is a known to prevent the activation of the AhR by UVB radiation and is described by the following formulae:

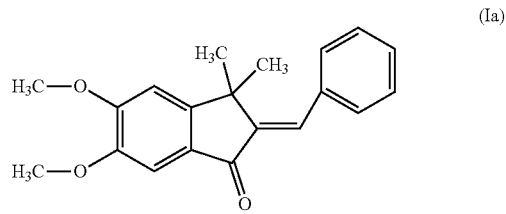

(Ia)

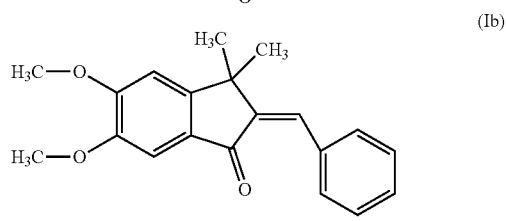

(Ib)

Benzylidene Dimethoxydimethylindanone

The product is obtainable under the trademark SymUrban™ from Symrise AG, Holzminden (DE).

Sclareolide

Sclareolide (CAS Number 564-20-5)

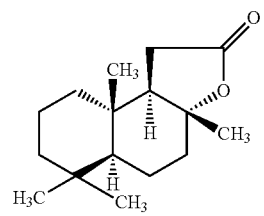

is a compound prepared by chemical modification or by biotransformation of the labdan type diterpene sclareol. Sclareol is present in stems, leaves and flowering parts of clary sage (Salvia sclarea L.) and its isolation from this source has been described (U.S. Pat. No. 3,060,172). According to the present invention, the source of sclareolide can be derived (extracted) naturally from either species of the Salvia genus, or can be synthetically obtained as substantially pure sclareolide. The substantially pure sclareolide contains according to the present invention more than 70 percent sclareolide.

Synonyms for Sclareolide are (3aR,5aS,9aS,9bR)-decahydro-3a,6,6,9a-tetramethyl-naphtha[2,1-b]furan-2(1H)- one; 3a,4,5,5aα,6,7,8,9,9a,9bα-decahydro-3aβ,6,6,9aβ-tetramethyl-naphtho[2,1-b]furan-2(1H)-one; [3aR-(3aα,5aβ,9aα,9bβ)]-decahydro-3a,6,6,9a-tetramethyl-Naphtho[2,1-b]furan-2(1H)-one; Norambreinolide; (+)-Norambreinolide; (+)-Sclareolide, (R)-(+)-Sclareolide; 13,14,15,16-Tetranor-labdano-8α,12-lactone; Norambreinolid.

Sclareolide is a precursor of ambroxan, a valuable ambergris fragrance used in perfumery. But as sclareolide is used itself as a fragrance material it is often a component of cosmetic formulations.

The anti-inflammatory activity of sclareol and sclareolide is described in WO 200 230385 A2 (Henkel). The anti-inflammatory activity is proven by an inhibition of 5-lipoxygenase as well as cyclooxygenase-1 activity. The use of Sclareolide within a natural combination of five components to treat acne is given in US 2003 072777 (Color Access). The anti-microbial activity of inter alia sclareolide and sclareol is already described in WO 1999 063978 A1 (Reynolds) concluding that sclareolide and sclareol are useful to treat acne, dermatitis and undesirable body odour. In WO 2001 074327 A2 (Color Access) the use of inter alia sclareolide as cell differentiation enhancer is disclosed. According to this patent the differentiation enhancers like sclareolide are used to stimulate the production of lipids from epidermal cells, and concurrently increase the lipid content of the barrier. As a use of the described compositions the enhancement and prolongation of self-tanning products is mentioned. Again the strengthening of barrier by the use of sclareolide alone as well as combined with white birch extract is described in WO 2002060381 A2 (Color Access). The use of sclareolide in cosmetic formulations used to enhance the stratum corneum function is described in US 2010 247692 A1 (Color Access). The invention WO 2008 155048 A1 (Cognis) discloses cosmetic compositions comprising sclareolide alone or combined with hesperidin methyl chalcone. The cosmetic compositions are described to be used for the tanning of skin, the darkening of hair, or the preventing of greying of hair.

Cosmetic Composition

Another object of the present invention encompasses cosmetic compositions comprising said actives. The compositions according to the present invention may represent personal care compositions, skin care compositions, hair care compositions or sun care compositions, for example in the form of a lotion, a cream, an emulsion, a foam, a mousse, an oil or a stick. Said compositions may contain said agents, binary or ternary mixtures in amounts of from about 0.01% by weight to about 2.5% by weight and preferably from about 0.05% by weight to about 1.0% by weight—calculated on the final composition.

Preferably, the compositions may further comprise cosmetically acceptable carriers, such as for example water, C2-C4 alcohols, polyols having 2 to 6 carbon atoms and/or oil bodies.

The preparations according to the invention may contain abrasives, anti-acne agents, agents against ageing of the skin, anti-cellulite agents, antidandruff agents, anti-inflammatory agents, irritation-preventing agents, irritation-inhibiting agents, antioxidants, astringents, perspiration-inhibiting agents, antiseptic agents, anti-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactants

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglycerde (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineraloladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkyl hydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxytearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations.

The preferred emulsifiers are described in more detail as follows:

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric Emulsifiers.

Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin deriva-tives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-phenylbenzimidazole sulfonic acid and salts (Neo Heliopan®Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan®MBC)
3-benzylidene-D,L-camphor
N-[(2 and 4)-[2-(oxoborn-3-ylidene) methyl]benzyl] acrylamide polymer
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb®HEB)
benzylidene malonate polysiloxane (Parsol®SLX)
glyceryl ethylhexanoate dimethoxycinnamate
dipropylene glycol salicylate
tris(2-ethylhexyl)-4,4',4"-(1,3,5-triazine-2,4,6-triyltriimino) tribenzoate (=2,4,6-trianilino-(p-carbo-2'-ethylhexyl-1'-oxy)-1,3,5-triazine) (Uvinul®T150).

Broadband filters which are preferably combined with one or more compounds of formula (I) in a preparation according to the present invention are selected from the group consisting of
2-ethylhexyl-2-cyano-3,3-diphenyl acrylate (Neo Heliopan®303)
ethyl-2-cyano-3,3'-diphenyl acrylate
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone
phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl®XL)
2,2'-methylene bis-(6-(2H-benzotriazol-2-yl)-4-1,1,3,3-tetramethylbutyl) phenol) (Tinosorb®M)
2,4-bis-[4-(2-ethylhexyloxy)-2-hydroxyphenyl]-1,3,5-triazine 2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethylhexyloxy)-2-hydroxy}phenyl]-6-[4-(2-methoxyethyl carbonyl) phenylamino]-1,3,5-triazine
2,4-bis-[{4-(3-(2-propyloxy)-2-hydroxypropyloxy)-2-hydroxy}phenyl]-6-[4-(2-ethylcarboxyl) phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2"-methylpropenyloxy)-2-hydroxy}phenyl]-6-(4-methoxyphenyl)-1,3,5-triazine
2,4-bis-[{4-(1',1',1',3',5',5',5'-heptamethylsiloxy-2"-methylpropyloxy)-2-hydroxy}phenyl]-6-(4-methoxyphenyl)-1,3,5-triazine.

The compositions can comprise further typical detergent and cleansing composition ingredients such as UV-A filters which are preferably combined with one or more compounds of formula (I) in a preparation according to the present invention are selected from the group consisting of
4-isopropyl dibenzoyl methane
terephthalylidene dibornane sulfonic acid and salts (Mexoryl®SX)
4-t-butyl-4'-methoxydibenzoyl methane (avobenzone)/(Neo Heliopan®357)
phenylene bis-benzimidazyl tetrasulfonic acid disodium salt (Neo Heliopan®AP)
2,2'-(1,4-phenylene)-bis-(1H-benzimidazole-4,6-disulfonic acid), monosodium salt
2-(4-diethylamino-2-hydroxybenzoyl) benzoic acid hexyl ester (Uvinul® A Plus)
indanylidene compounds in accordance with DE 100 55 940 A1 (=WO 2002 038537 A1)

The compositions can comprise further typical detergent and cleansing composition ingredients such as UV filters which are more preferably combined with one or more compounds of formula (I) in a preparation according to the present invention are selected from the group consisting of
p-aminobenzoic acid
3-(4'-trimethylammonium) benzylidene bornan-2-one methyl sulfate
salicylic acid homomenthyl ester (Neo Heliopan®R HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene) methyl]benzyl] acrylamide polymer
p-methoxycinnamic acid-2-ethylhexyl ester (Neo Heliopan®AV)
p-aminobenzoic acid ethyl ester (25 mol) ethoxylated (INCI name: PEG-25 PABA)
p-methoxycinnamic acid isoamyl ester (Neo Heliopan®E1000)
2,4,6-trianilino-(p-carbo-2'-ethylhexyl-1'-oxy)-1,3,5-triazine (Uvinul® T150)
phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl®XL)
4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl) phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine (Tinosorb®S)
benzylidene malonate polysiloxane (Parsol® SLX)
menthyl anthranilate (Neo Heliopan®MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin and/or Hair Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of *rumex* and *ramulus* species, extracts of pine species (*pinus*), extracts of *vitis* species or stilbene derivatives isolated or concentrated therefrom, saxifrage extract, scutelleria extract, grape extract and/or microalgae extract, in particular Tetraselmis suecica Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and ana-logues thereof, activators of adenylate cyclase and compounds which activate the transfer of melanosomes to keratinocytes such as serine proteases or agonists of the PAR-2 receptor, extracts of plants and plant parts of the chrysanthemum species, san-guisorba species, walnut extracts, urucum extracts, rhubarb extracts, microalgae extracts, in particular *Isochrysis galbana*, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actives

In the context of the invention, anti-ageing or biogenic agents are, for example antioxidants, matrix-metalloproteinase inhibitors (MMPI), skin moisturizing agents, glycosaminglycan stimulkators, anti-inflammatory agents, TRPV1 antagonists and plant extracts.

Antioxidants.

Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, ZnSO$_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, *sophora, pueraria, pinus,* citrus, *Phyllanthus emblica* or St. John's wort, grape seeds, wheat germ, *Phyllanthus emblica,* coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-Moisturizing Agents.

Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan Stimulators.

Preferred compositions comprise substances stimulating the synthesis of glycosaminoglycans selected from the group consisting of hyaluronic acid and derivatives or salts, Subliskin (Sederma, INCI: Sinorhizobium Meliloti Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, Sinorhizobium Meliloti Ferment Filtrate, Calcium ketogluconate, *Alpinia galanga* leaf extract and tetradecyl aminobutyroylvalylaminobutyric urea trifluoroacetate.

Anti-Inflammatory Agents.

The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, calendula, *arnica*, St John's wort, honeysuckle, rosemary, *Passiflora incarnata*, witch hazel, ginger or *Echinacea*; preferably selected from the group consisting of extracts or fractions from camomile, Aloe vera, oats, calendula, *arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

Desquamating Agents.

The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SI LAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-Cellulite Agents.

Anti-cellulite agents and lipolytic agents are preferably selected from the group consisting of those described in WO 2007/077541, and beta-adrenergic receptor agonists such as Synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzyme A, isoflavonoides, soy extracts, ananas extract and conjugated linoleic acid.

Fat Enhancing Agents.

Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrinnidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxacum*), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, Isochrysis galbana*, licorice, grape, apple, barley or hops or/and hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre*.

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (1-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^{\alpha}$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(−)-isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, *galbanum* oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, *angelica*, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (*galbanum*, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, *galbanum* oil, *ladanum* oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3Fe_3O_4$, FeO(OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

Medicament

Another object of the present invention refers to a medicament comprising an anti-pollution agent selected from the group consisting of purple coneflower pressed juice, sclareolide, ginger root CO2 extract, E/Z-2-benzylindene-5,6-dimethoxy-3,3-dimethylindan-1-one, especially preferred purple coneflower pressed juice or a preferred binary or ternary mixture as described aforementioned for protecting, preventing, treating and/or curing human skin and/or hair from disorders and dysfunctions associated with
(a) air pollution induced gene expression, and/or
(b) gene expression induced or inducible by polycyclic aromatic hydrocarbons, and/or
(c) air pollution-induced or air pollution-inducible skin damage.

In particular, the protection and prevention from air pollution induced disorders and dysfunctions to skin and/or hair especially refers to the inhibition of the induction of
1) POMC gene, and therefore protects skin cells against excessive melanin formation; and/or
2) MMP1 (matrixmetalloproteinase-1) in the skin to protect the skin against increased formation of wrinkles; and/or
3) IL-6 (interleukin-6) to protect skin cells against inflammation as well as pigment spot formation, wherein the inflammation is in particular not based on fungal infection and/or
4) CYPA1 gene expression to protect skin cells against damages due to AhR activation, particularly particle induced CYP1A1 gene expression.

Non-Therapeutical Method

Another object of the present invention refers to a non-therapeutical method for protecting human skin and/or hair against air pollution induced damages by applying an effective amount of at least one anti-pollution agent selected from the group consisting of purple coneflower pressed juice, sclareolide, ginger root CO2 extract, E/Z-2-benzylindene-5, 6-dimethoxy-3,3-dimethylindan-1-one, especially preferred purple coneflower pressed juice or a preferred binary or ternary mixture as described aforementioned.

Preferably 0.1 mg/cm$^2$ to about 5 mg/cm$^2$, preferably 2 mg/cm$^2$ to 3 mg/cm$^2$ of a formulation containing from about 0.1% by weight to 0.5% by weight, preferably from 0.3% by weight to 0.5% by weight of said active agents of the present invention, are applied to human skin and/or hair, which is an effective amount of about 8 µg/cm$^2$ to about 10 µg/cm$^2$ of said agents.

Use

A final object of the present invention is directed to the use of an anti-pollution agent selected from the group consisting of purple coneflower pressed juice, sclareolide, ginger root CO2 extract E/Z-2-benzylindene-5,6-dimethoxy-3,3-dimethylindan-1-one, especially preferred purple coneflower pressed juice or a preferred binary or ternary mixture as described aforementioned for protecting human skin and/or hair against air pollution.

Another important object of the invention is the use of purple coneflower pressed juice or a binary mixture or a ternary mixture or a preferred binary or ternary mixture as described aforementioned as AhR antagonist.

In particular, the protection of human skin and/or hair against air pollution is directed to air pollution induced through the induction of certain genes, which lead to melanin formation and/or wrinkle formation and/or inflammation, respectively pigment spot formation, wherein the inflammation is in particular not based on fungal infection, and/or diseases associated with AhR activation measured as CYP1A1 gene expression upregulation, particularly particle induced CYP1A1 gene expression.

Thus more preferably the invention is directed to the use of an anti-pollution agent selected from the group consisting of purple coneflower pressed juice, sclareolide, ginger root CO2 extract, E/Z-2-benzylindene-5,6-dimethoxy-3,3-dimethylindan-1-one, especially preferred purple coneflower pressed juice or a preferred binary or ternary mixture as described aforementioned for protecting and/or inhibiting and/or reducing of disorders and dysfunctions of human skin and hair related to, respectively associated with the induction of POMC gene and/or, MMP1 gene and/or IL-6 gene, and/or particle induced CYP1A1 gene expression, particularly preferred hereby is ginger root CO2 extract.

A particular preferred aspect of the present invention is the use of a preferred binary or ternary mixture as described above for protecting and/or inhibiting and/or reducing of disorders and dysfunctions of human skin and hair related to, respectively associated with the induction of POMC gene expression and/or, MMP1 gene expression and/or IL-6 gene expression, and/or particle induced CYP1A1 gene expression, particularly preferred is a binary mixture comprising purple coneflower pressed juice and ginger root CO2 extract or sclareolide or also preferred is a ternary mixture comprising purple coneflower pressed juice and sclareolide and ginger root CO2 extract.

Preferably 0.1 mg/cm$^2$ to about 5 mg/cm$^2$, preferably 2 mg/cm$^2$ to 3 mg/cm$^2$ of a formulation containing from about 0.1% by weight to 0.5% by weight, preferably from 0.3% by weight to 0.5% by weight of said active agents of the present invention, are applied to human skin and/or hair, which is an effective amount of about 8 μg/cm² to about 10 μg/cm² of said agents.

Another object of the invention is the use of a compound selected from purple coneflower pressed juice, sclareolide, ginger root CO2 extract, E/Z-2-benzylindene-5,6-dimethoxy-3,3-dimethylindan-1-one, especially preferred purple coneflower pressed juice or a binary mixture as listed aforementioned or a ternary mixture as listed aforementioned as anti-pollution agent, respectively anti-pollution mixture for protecting human skin and/or hair, especially protecting and/or inhibiting and/or reducing of disorders and dysfunctions of human skin and hair related to, respectively associated with the induction of POMC gene expression and/or, MMP1 gene expression and/or IL-6 gene expression and/or particle induced CYP1A1 gene expression. Particularly preferred is purple coneflower pressed juice or a binary mixture comprising purple coneflower pressed juice and ginger root CO2 extract or sclareolide or also preferred is a ternary mixture comprising purple coneflower pressed juice and sclareolide and ginger root CO2 extract.

Further object of the present invention is a non-therapeutical use of at least an agent selected from the group consisting of purple coneflower pressed juice, sclareolide, ginger root CO2 extract, E/Z-2-benzylindene-5,6-dimethoxy-3,3-dimethylindan-1-one, especially preferred purple coneflower pressed juice or a binary mixture or a ternary mixture of these agents as described aforementioned in a cosmetic composition, in an amount from about 0.01% by weight to about 2.5% by weight, preferably from about 0.05% by weight to about 1.0% by weight, as anti-pollution agent, respectively anti-pollution mixture for protecting human skin and hair, especially protecting and/or inhibiting and/or reducing of disorders and dysfunctions of human skin and hair related to, respectively associated with the induction of POMC gene expression and/or, MMP1 gene expression and/or IL-6 gene expression and/or particle induced CYP1A1 gene expression. Particularly preferred is purple coneflower pressed juice or a binary mixture comprising purple coneflower pressed juice and ginger root CO2 extract or sclareolide or also preferred is a ternary mixture comprising purple coneflower pressed juice and sclareolide and ginger root CO2 extract.

EXAMPLES

Example 1

Model Particles

Gene expression was induced by different model particles. SRM 1650b and SRM 2975 are surrogates for authentic street particulate matter (Danielson et al, 2008). Fine carbon black is a model particle for indoor pollution, e.g. particles from laser printers. The details are set out in Table 1:

TABLE 1

Model particles applied in vitro to induce gene expression

| Type | Name | Source |
| --- | --- | --- |
| Diesel exhaust particle | SRM1650b | National Institute of Standards and Technology, Gaithersburg, MD, USA |
| Diesel exhaust particle | SRM2975 | National Institute of Standards and Technology, Gaithersburg, MD, USA |
| Fine carbon black | Huber 990 | Evonik Industries, Essen, Germany |

Example 2

Anti-Air Pollution activity of E/Z-2-benzylindene-5,6-dimethoxy-3,3-dimethylindan-1-one Adult human epidermal keratinocytes were cultured in keratinocyte medium without BPE and without EGF for 24 h prior to addition of model particles (see table 1.1). The model particles were suspended in phosphate buffered saline and were sonicated for 1 min and then directly added to the keratinocytes at 1.5 μg/cm². E/Z-2-benzylindene-5,6-dimethoxy-3,3-dimethylindan-1-one (BDDI) has been dissolved in DMSO and diluted in medium. Solutions containing the compound with maximal 0.1% DMSO were applied 2 h prior to treatment with the model particles. Gene expression was analyzed via qRT-PCR. For each gene, a specific PCR primer pair was designed as compiled in Table 2:

TABLE 2

Specific primer pairs for RT-PCR (forward/reverse)

| | |
| --- | --- |
| 18S | 5'-GCCGCTAGAGGTGAAATTCTTG-3' |
| | 5'-CATTCTTGGCAAATGCTTTCG'-3' |
| CYP1A1 | 5'-AGATGGTCAAGGAGCACTACAAAA-3' |
| | 5'-GCTCAATCAGGCTGTCTGTGAT-3' |
| IL-6 | 5'-CCTCGAGCCCACCGGGAACG-3' |
| | 5'-AACTGGACCGAAGGCGCTTGTG-3' |
| POMC | 5'-TGGAAGTGCGTGGCTGGT-3' |
| | 5'-TGCACTCCAGCAGGTTGCT-3' |
| MMP1 | 5'-TGAAAGGTGGACCAACAATTT-3' |
| | 5'-CCAAGAGAATGGCCGAGTTC-3' |

CYP1A1: cytochrome P450 1A1; IL-6: Interleukin 6; POMC: proopiomelanocortin; MMP1: matrix metalloproteinase 1

The following Tables 3 and 4 show the results for CYP1A1 gene expression after induction with outdoor and indoor particles, Table 5 POMC, IL-6 and MMP1 expression.

TABLE 3

CYP1A1 gene expression after induction with outdoor particles

| Compound | Time | Noxae | Particle conc. | CYP1A1 Induction mean ± SE | |
| --- | --- | --- | --- | --- | --- |
| NHEK: adult, female, Asian | | | | | |
| untreated | | | | 1 | |
| | 6 h | SRM1650 | 1.5 μg/cm2 | 5.33 ± 0.07 | * |
| 10 μM BDDI | 6 h | SRM1650 | 1.5 μg/cm2 | 1.83 ± 0.03 | + |
| | 24 h | SRM1650 | 1.5 μg/cm2 | 16.53 ± 0.98 | * |

TABLE 3-continued

CYP1A1 gene expression after induction with outdoor particles

| Compound | Time | Noxae | Particle conc. | CYP1A1 Induction mean ± SE | |
|---|---|---|---|---|---|
| 10 µM BDDI untreated | 24 h | SRM1650 | 1.5 µg/cm2 | 4.17 ± 0.09 | + |
|  | 6 h | SRM2975 | 1.5 µg/cm2 | 1 2.07 ± 0.07 | * |
| 10 µM BDDI | 6 h | SRM2975 | 1.5 µg/cm2 | 0.05 ± 0.0003 | + |
|  | 24 h | SRM2975 | 1.5 µg/cm2 | 4.90 ± 0.17 | * |
| 10 µM BDDI untreated | 24 h | SRM2975 | 1.5 µg/cm2 | 0.01 ± 0.00 1 | + |
|  | 6 h | SRM2975 | 1.5 µg/cm2 | 4.9 ± 0.17 | * |
| 10 µM Sclareolide | 6 h | SRM2975 | 1.5 µg/cm2 | 0.4 ± 0 | + |
|  | 6 h | SRM1650b | 1.5 µg/cm2 | 16.53 ± 0.98 | * |
| 10 µM Sclareolide | 6 h | SRM1650b | 1.5 µg/cm2 | 2.73 ± 0.03 | + |
| NHEK: adult, female, Caucasian | | | | | |
| untreated | | | | 1 | |
|  | 6 h | SRM1650 | 1.5 µg/cm2 | 2.90 ± 0.12 | * |
| 10 µM BDDI | 6 h | SRM1650 | 1.5 µg/cm2 | 0.02 ± 0.00 | + |
|  | 24 h | SRM1650 | 1.5 µg/cm2 | 23.23 ± 0.64 | * |
| 10 µM BDDI untreated | 24 h | SRM1650 | 1.5 µg/cm2 | 8.77 ± 0.09 1 | + |
|  | 6 h | SRM2975 | 1.5 µg/cm2 | 1.03 ± 0.03 | n.s. |
| 10 µM BDDI | 6 h | SRM2975 | 1.5 µg/cm2 | 0.20 ± 0.00 | + |
|  | 24 h | SRM2975 | 1.5 µg/cm2 | 5.10 ± 0.06 | * |
| 10 µM BDDI untreated | 24 h | SRM2975 | 1.5 µg/cm2 | 0.60 ± 0.06 1 | + |
|  | 6 h | SRM2975 | 1.5 µg/cm2 | 5.1 ± 0.06 | * |
| 10 µM Sclareolide | 6 h | SRM2975 | 1.5 µg/cm2 | 0.47 ± 0.03 | + |
|  | 6 h | SRM1650b | 1.5 µg/cm2 | 23.23 ± 0.64 | * |
| 10 µM Sclareolide | 6 h | SRM1650b | 1.5 µg/cm2 | 2.87 ± 0.12 | + |

*significant versus untreated, p < 0.05;
+ significant versus stimulated control (SRM1650b), p < 0.05;
n.s. not significant

TABLE 4

CYP1A1 gene expression after induction with indoor particles

| Compound | Time | Noxae | Particle conc. | Induction mean ± SE | |
|---|---|---|---|---|---|
| untreated | | | | 1 | |
|  | 6 h | Huber990 | 1.5 µg/cm2 | 2.70 ± 0.00 | * |
| 10 µM BDDI | 6 h | Huber990 | 1.5 µg/cm2 | 0.05 ± 0.00 | + |
|  | 24 h | Huber990 | 1.5 µg/cm2 | 2.90 ± 0.00 | * |
| 10 µM BDDI | 24 h | Huber990 | 1.5 µg/cm2 | 0.20 ± 0.00 | + |

*significant versus untreated, p < 0.05;
+ significant versus stimulated control (SRM1650b), p < 0.05

TABLE 5

POMC, IL-6 and MMP1 gene expression

| Comp. | c. | | POMC 6 h | | IL-6 6 h | | MMP1 24 h | |
|---|---|---|---|---|---|---|---|---|
| Control | | | 1 | | 1 | | 1 | |
|  | | SRM1650b | 1.5 ± 0.031 | * | 1.4 ± 0.041 | * | 1.3 ± 0.03 | * |
| BDDI | 10 µM | SRM1650b | 0.9 ± 0.001 | + | 0.5 ± 0.01 | n.s. | 0.5 ± 0.022 | + |
| BDDI | 2.5 µM | SRM1650b | 1.1 ± 0.02 | + | 0.6 ± 0.006 | n.s. | 0.8 ± 0.016 | + |
| BDDI | 1 µM | SRM1650b | 0.9 ± 0.018 | + | 0.9 ± 0.067 | n.s. | 0.7 ± 0.014 | + |

* significant versus untreated, p < 0.05;
+ significant versus stimulated control (SRM1650b), p < 0.05

E/Z-2-benzylindene-5,6-dimethoxy-3,3-dimethylindan-1-one was capable to inhibit particle induced Cyp1A1 gene expression. It was shown for indoor as well as outdoor model particles. E/Z-2-benzylindene-5,6-dimethoxy-3,3-dimethylindan-1-one was also capable to inhibit particle induced POMC, IL-6 and MMP1 gene expression.

Example 3

Anti-Air Pollution Activity of Sclareolide

Adult human epidermal keratinocytes were cultured in keratinocyte medium without BPE and without EGF for 24 h prior to addition of model particles (see table 1.1). The model particles were suspended in phosphate buffered saline and were sonicated for 1 min and then directly added to the keratinocytes at 1.5 µg/cm². Sclareolide has been dissolved in DMSO and diluted in medium. Solutions containing the compound with maximal 0.1% DMSO were applied 2 h prior to treatment with the model particles. Gene expression was analyzed via qRT-PCR. For each gene, a specific PCR primer pair was designed (see Table 2). Table 6 compiles the results for sclareolide altered POMC gene expression.

TABLE 6

Sclareolide altered POMC gene expression

| Compound | conc. | noxae | POMC 24 h | |
|---|---|---|---|---|
| untreated | | | 1 | |
| | | SRM1650b | 1.50 ± 0.06 | * |
| Sclareolide | 10 µM | SRM1650b | 1.03 ± 0.07 | + |
| | | SRM2975 | 1.30 ± 0.00 | * |
| Sclareolide | 10 µM | SRM2975 | 0.73 ± 0.06 | + |

* significant versus untreated, p < 0.05;
+ significant versus stimulated control (SRM1650b), p < 0.05

Sclareolide was capable to inhibit particle induced POMC gene expression.

Example 4

Anti-Air Pollution Activity of Ginger Root CO2 Extract

Adult human epidermal keratinocytes were cultured in keratinocyte medium without BPE and without EGF for 24 h prior to addition of model particles (see table 1.1). The model particles were suspended in phosphate buffered saline and were sonicated for 1 min and then directly added to the keratinocytes at 1.5 µg/cm$^2$. Ginger root CO2 extract has been dissolved in DMSO and diluted in medium. Solutions containing the compound with maximal 0.1% DMSO were applied 2 h prior to treatment with the model particles. Gene expression was analyzed via qRT-PCR. For each gene, a specific PCR primer pair was designed (see Table 2). Table 7 compiles the results for ginger root CO2 extract altered POMC and IL-6 gene expression

TABLE 7

Ginger root CO2 extract altered POMC and IL-6 gene expression

| Compound | conc. | noxae | POMC 6 h | | IL-6 6 h | |
|---|---|---|---|---|---|---|
| untreated | | | 1 | | 1 | |
| | | SRM1650b | 1.5 ± 0.031 | * | 1.4 ± 0.041 | * |
| ginger root CO2 extract | 0.0001% | SRM1650b | 1.1 ± 0.017 | + | 0.5 ± 0.013 | + |
| ginger root CO2 extract | 0.00002% | SRM1650b | 0.8 ± 0.016 | + | 0.8 ± 0.015 | + |
| ginger root CO2 extract | 0.000004% | SRM1650b | 0.8 ± 0.048 | + | 0.9 ± 0.018 | + |

* significant versus untreated, <0.05;
+ significant versus stimulated control (SRM1650b), <0.05

Ginger root CO2 extract was capable to inhibit particle induced POMC and IL-6 gene expression.

Example 5

Anti-Air Pollution Activity of Purple Coneflower Pressed Juice

Adult human epidermal keratinocytes were cultured in keratinocyte medium without BPE and without EGF for 24 h prior to addition of model particles (see table 1.1). The model particles were suspended in phosphate buffered saline and were sonicated for 1 min and then directly added to the keratinocytes at 1.5 µg/cm$^2$. Purple coneflower pressed juice has been dissolved directly in medium. The solutions were applied 2 h prior to treatment with the model particles. Gene expression was analyzed via qRT-PCR. For each gene, a specific PCR primer pair was designed (see Table 2). Table 8 compiles the results for purple coneflower pressed juice altered POMC and IL-6 gene expression

TABLE 8

Purple coneflower pressed juice altered POMC and IL-6 gene expression

| Compound | conc. | noxae | POMC 24 h | | IL-6 6 h | |
|---|---|---|---|---|---|---|
| untreated | | | 1 | | 1 | |
| | | SRM1650b | 1.56 ± 0.07 | * | 1.39 ± 0.01 | * |
| purple coneflower pressed juice | 0.01% | SRM1650b | 0.34 ± 0.006 | + | 1.06 ± 0.03 | + |

TABLE 8-continued

Purple coneflower pressed juice altered POMC and IL-6 gene expression

| Compound | conc. | noxae | POMC 24 h | | IL-6 6 h | |
|---|---|---|---|---|---|---|
| purple coneflower pressed juice | 0.002% | SRM1650b | 0.36 ± 0.01 | + | 1.26 ± 0.03 | + |
| purple coneflower pressed juice | 0.0004% | SRM1650b | 0.44 ± 0.02 | + | 0.49 ± 0.01 | + |

\* significant versus untreated, <0.05;
+ significant versus stimulated control (SRM1650b), <0.05

Purple coneflower pressed juice was capable to inhibit particle induced POMC and IL-6 gene expression.

Example 6

Anti-Air Pollution Activity of a Binary Mixture

Adult human epidermal keratinocytes were cultured in keratinocyte medium without BPE and without EGF for 24 h prior to addition of model particles (see table 1.1). The model particles were suspended in phosphate buffered saline and were sonicated for 1 min and then directly added to the keratinocytes at 1.5 mg/cm$^2$. A mixture of purple coneflower pressed juice and ginger root CO2 extract has been pre-dissolved in DMSO and diluted in medium. The solutions were applied 2 h prior to treatment with the model particles. Gene expression was analyzed via qRT-PCR. For each gene, a specific PCR primer pair was designed (see Table 2). Table 9 compiles the results for purple coneflower pressed juice altered POMC and IL-6 gene expression

TABLE 9

Binary mixture of purple coneflower pressed juice and ginger root CO2 extract altered POMC and IL-6 gene expression

| Compound | conc. | noxae | POMC 6 h | | IL-6 6 h | |
|---|---|---|---|---|---|---|
| untreated | | | 1 | | 1 | |
| | | SRM1650b | 1.5 ± 0.03 | * | 1.4 ± 0.041 | * |
| Binary mixture | 0.0004% | SRM1650b | 0.9 ± 0.03 | + | 1.1 ± 0.07 | + |
| Binary mixture | 0.0001% | SRM1650b | 1.1 ± 0.09 | + | 1.2 ± 0.09 | + |
| Binary mixture | 0.00004% | SRM1650b | 1.3 ± 0.12 | | 1.2 ± 0.08 | |

\* significant versus untreated, <0.05;
+ significant versus stimulated control (SRM1650b), <0.05

Binary mixture was capable to inhibit particle induced POMC and IL-6 gene expression.

Examples 7 to 17

Skin and Hair Care Preparations
In the following the present invention is illustrated in more detail by various formulation examples:
7=Skin Care Gel (SPF 6)
8=Sun Protection Lotion SPF 24 (UVA/UVB Balance)
9=Tinted Anti-aging Balm, SPF 15
10=Body Lotion, SPF 15
11=Skin Soothing Night Cream O/W
12=Cream W/O
13=Skin Care Ampoule
14=Skin Oil
15=Shower & Shampoo
16=Tinted Skin Care Stick SPF 50
17=Hair Gel In Formulation Examples 7-17 the following two perfume oils PFO1 and PFO2 were each used as fragrance (DPG=dipropylene glycol).

TABLE A

Perfume oil PFO1 with rose smell (amounts in parts b.w.)

| Component | Amount |
|---|---|
| Acetophenone, 10% in DPG | 10.00 |
| n-Undecanal | 5.00 |
| Aldehyde C14, so-called (peach aldehyde) | 15.00 |
| Allylamyl glycolate, 10% in DPG | 20.00 |
| Amyl salicylate | 25.00 |
| Benzyl acetate | 60.00 |
| Citronellol | 80.00 |
| d-Limonene | 50.00 |
| Decenol trans-9 | 15.00 |
| Dihydromyrcenol | 50.00 |
| Dimethylbenzylcarbinyl acetate | 30.00 |
| Diphenyloxide | 5.00 |
| Eucalyptol | 10.00 |
| Geraniol | 40.00 |
| Nerol | 20.00 |
| Geranium oil | 15.00 |
| Hexenol cis-3, 10% in DPG | 5.00 |
| Hexenyl salicylate cis-3 | 20.00 |
| Indole, 10% in DPG | 10.00 |
| Alpha-ionone | 15.00 |
| Beta-ionone | 5.00 |
| Lilial ® (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrolyl acetate | 20.00 |
| Terpineol | 30.00 |
| Tetrahydrolinalool | 50.00 |
| Cinnamyl alcohol | 10.00 |
| Total: | 1,000.00 |

TABLE B

Perfume oil PFO2 with white blossom and musk smell (amounts in parts b.w.)

| Component | Amount |
|---|---|
| Benzyl acetate | 60.00 |
| Citronellyl acetate | 60.00 |
| Cyclamenaldehyde (2-methyl-3-(4-isopropylphenyl)propanal | 20.00 |
| Dipropylene glycol (DPG) | 60.00 |
| Ethyllinalool | 40.00 |
| Florol (2-isobutyl-4-methyltetrahydro-2H-pyran-4-ol) | 30.00 |
| Globanone ® [(E/Z)-8-cyclohexadecen-1-one] | 180.00 |
| Hedione ® (methyldihydrojasmonate) | 140.00 |
| Hexenyl salicylate, cis-3 | 10.00 |

TABLE B-continued

Perfume oil PFO2 with white blossom and musk smell (amounts in parts b.w.)

| Component | Amount |
|---|---|
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalyl acetate | 30.00 |
| Methyl benzoate, 10% in DPG | 25.00 |
| para-Methyl cresol, 10% in DPG | 10.00 |
| Nerol | 20.00 |
| Phenylpropylaldehyde | 5.00 |
| 2-Phenylethyl alcohol | 82.00 |
| Tetrahydrogeraniol | 13.00 |
| 2,2-Dimethyl-3-cyclohexyl-1-propanol | 80.00 |
| Total: | 1,000.00 |

TABLE 9

Air pollution protecting compositions

| Ingredients | INCI-Name | 7 | 8 | 9 | 10 | 11 | 12 | 13 | 14 | 15 | 16 | 17 |
|---|---|---|---|---|---|---|---|---|---|---|---|---|
| SymHelios ®1031 | Benzylidene Dimethoxydimethylindanone | 0.5 | 0.3 | | 0.1 | | | | | 0.5 | 0.5 | |
| Sclareolide | Sclareolide | 0.1 | | | | | 0.5 | | 0.05 | | | 0.1 |
| SymFinity ® 1298 | *Echinacea Purpurea* Extract | | | 0.4 | | 0.5 | | | | | | |
| SymVital ® AgeRepair 3040 | *Zingiber Officinale* (Ginger) Root Extract | | 0.05 | 0.1 | | | | 0.2 | 0.1 | | | 0.2 |
| (−) alpha Bisabolol nat. | Bisabolol | | 0.1 | | 0.2 | | | | | | 0.1 | |
| Abil 350 | Dimethicone | | | 2 | | | | | | | | |
| Actipone ® *Laminaria Saccharina* GW | Glycerin, Water (Aqua), *Laminaria Saccharina* Extract | | | | | 1 | | | | | | |
| *Aloe Vera* Gel Conc.10:1 | *Aloe Barbadensis* Leaf Juice | | 1 | | | | | | | | | |
| Aluminium Stearate | Aluminium Stearate | | | | | | | | 1.2 | | | |
| Amaze XT | Dehydroxanthan Gum | 1.4 | | | | | | | | | | |
| beta-Arbutin | Arbutin | | | | | 0.5 | | | | | | |
| Betulin 90% (1079) | Betulin | | | | | 0.15 | | | | | | |
| Biotive ® L-Arginine | Arginine | 3.2 | 0.5 | 0.6 | 0.9 | | | | | | | |
| Biotive ® Troxerutin | Troxerutin | | 0.5 | 0.5 | | | | | | | | |
| Carbopol ETD 2020 | Acrylates/C10-30 Alkyl Acrylate Crosspolymer | 0.2 | | | | | | | | | | |
| Carbopol ETD 2050 | Carbomer | | | 0.2 | | 0.2 | | | | | | |
| Carbopol Ultrez-21 | Acrylates/C10-30 Alkyl Acrylate Crosspolymer | | | | 0.5 | | | | | | | |
| Citric Acid 10% sol. in water | Citric Acid | | | | | | | | | 3.1 | | |
| Comperlan 100 | Cocamide MEA | | | | | | | | | 1 | | |
| Corapan TQ | Diethylhexyl 2,6 Naphtalate | | | | | | 3 | | | | | |
| Crinipan ® AD | Climbazole | | | | | | | | | | | 0.1 |
| Cutina GMS V | Glyceryl Stearate | | | | | | | 2 | | | | |
| Cutina PES | Pentaerythrityl Distearate | | | | 2 | | | | | | | |
| Cutina TS | PEG-3 Distearate | | | | | | | | | 2.5 | | |
| DC9701 Cosmetic Powder | Dimethicone/Vinyl Dimethicone Crosspolymer, Silica | | | | | | | | | | 2 | |
| Dermacryl AQF | Acrylates Copolymer | | | | 2 | | | | | | | |
| Dipropylene Glycol | Dipropylene Glycol | | | | | | | | | | | 1 |
| Dow Corning 193 surfactant | PEG-12 Dimethicone | 1 | | | | | | | | | | |
| Dow Corning 246 fluid | Cyclohexasiloxane | | | 3 | | 1 | | | | | | |

TABLE 9-continued

Air pollution protecting compositions

| Ingredients | INCI-Name | 7 | 8 | 9 | 10 | 11 | 12 | 13 | 14 | 15 | 16 | 17 |
|---|---|---|---|---|---|---|---|---|---|---|---|---|
| D-Panthenol 75 L | Panthenol | | | | | | | 1 | | 0.3 | | 0.5 |
| Dracorin ® CE | Glyceryl Stearate/Citrate | | | | | 3 | | | | | | |
| Dracorin ® GOC | Glyceryl Oleate Citrate, Caprylic Capric Triglyceride | | | | 1.5 | | | | | | 0.5 | |
| Drago-Beta-Glucan | Water (Aqua), Butylene Glycol, Glycerin, *Avena Sativa* (Oat) Kernel Extract | | | | | 1 | | | | | | |
| DragoCalm ® | Water, Glycerin, *Avena Sativa* (Oat Kernel Extract) | | | | | | | 1 | | | | |
| Dragoderm ® | Glycerin, *Triticum Vulgare* (Wheat) Gluten, Water (Aqua) | | | | | | 2 | | | | | |
| Dragosan W/O P | Sorbitan Isostearate, Hydrogenated Castor Oil, Ceresin, Beeswax (Cera Alba) | | | | | | | 8 | | | | |
| Dragosantol ® 100 | Bisabolol | | | 0.1 | | | 0.2 | | | | | |
| Dragosine ® | Carnosine | 0.2 | | | | | | 0.2 | | 15 | | |
| Dragoxat ® 89 | Ethylhexyl Isononanoate | | 2 | 5 | | 4 | 7 | | | 15 | 5 | |
| EDTA B | Tetrasodium EDTA | | | | | | | 0.1 | | | | |
| EDTA BD | Disodium EDTA | | 0.1 | 0.1 | 0.1 | | | | | | | 0.1 |
| Emulsiphos ® | Potassium Cetyl Phosphate, Hydrogenated Palm Glycerides | | 2 | 2 | | | | | | | | |
| Ethanol | Ethanol | 10 | | | | | | | | | | |
| Ethylhexyl Cyclohexyl Urea | Ethylhexyl Cyclohexyl Urea | | | | | | | 0.5 | | | | |
| Extrapone ® *Ginkgo Biloba* | Propylene Glycol, Water (Aqua), *Ginkgo Biloba* Leaf Extract, Glucose, Lactic Acid | | | | | 1 | | | | | | |
| Food Color Brown E172 + E171 Powder | Color | | | 2 | | | | | | | 3 | |
| Fragrance PFO1 or PFO2 | Parfum | 0.1 | 0.2 | 0.3 | 0.2 | 0.4 | 0.3 | 0.1 | 0.5 | 1 | | 0.1 |
| Frescolat ® MGA | Menthone Glycerin Acetal | | | | | | | 0.1 | | | | |
| Frescolat ® ML | Menthyl Lactate | | | | | | | | | | 0.2 | |
| Frescolat ® X-Cool | Menthyl Ethylamido Oxalate | | 0.4 | | | | | | | | | |
| Fruitapone ® Orange B | Propylene Glycol, Water (Aqua), Citric Acid, Citrus *Aurantium Dulcis* (Orange) Juice, Trideceth-9, Bisabolol | | | | | | | | | | | 0.5 |
| Glycerine 99.5% | Glycerin | 2.5 | 3 | | | 5 | 3 | | | 0.5 | | 10 |
| Hydrolite ®-5 | Pentylene Glycol | 3 | 2 | | 5 | | | | | 1 | | |
| Hydroviton ®-24 | Water, Pentylene Glycol, Glycerin, Lactic Acid, Sodium Lactate, Serine, Urea, Sorbitol, Sodium Chloride, Allantoin | | | | | 1 | 1 | | 10 | | | |
| Iso Adipat | Diisopropyl Adipate | | | | | 1 | | | | 5 | | |

TABLE 9-continued

Air pollution protecting compositions

| Ingredients | INCI-Name | 7 | 8 | 9 | 10 | 11 | 12 | 13 | 14 | 15 | 16 | 17 |
|---|---|---|---|---|---|---|---|---|---|---|---|---|
| Isodragol ® | Triisononanoin | | 2 | | | | | | | | | |
| Isopropyl Palmitate | Isopropyl Palmitate | | | | | | | | | | 13 | |
| Jaguar C-162 | Hydroxypropyl Guar, Hydroxypropyltrimonium Chloride | | | | | | | | | 0.1 | | |
| Jojoba Oil | Simmondsia Chinensis (Jojoba) Seed Oil | 1 | | | | | 2 | | | | | |
| Keltrol CG RD | Xanthan Gum | | 0.4 | 0.2 | 0.2 | 0.1 | | 0.05 | | | | 1 |
| Kojic acid | Kojic acid | 0.1 | | | | | | | | | | 1 |
| Lanette 16 | Cetyl Alcohol | | 1 | | | | | | | | | |
| Lanette O | Cetearyl Alcohol | | 0.5 | | | 3 | | | | | 5 | |
| Lara Care A-200 | Galactoarabinan | | 0.3 | | | | | | | | | |
| Luviskol K30 Powder | PVP | | | | | | | | | | | 3 |
| Magnesium ascorbyl phosphate | Magnesium ascorbyl phosphate | | | | 5 | | | | | | 3 | |
| Magnesium Sulfate | Magnesium Sulfate | | | | | | | 0.7 | | | | |
| Mineral Oil | Mineral Oil | | | | | | | 8 | ad 100 | | | |
| Neo Heliopan ® 303 | Octocrylene | | 10 | 4 | | | | | | | 10 | |
| Neo Heliopan ® 357 | Butylmethoxydibenzoylmethane | | 3 | 2 | 3 | | | | | | 5 | |
| Neo Heliopan ® AP | Disodium Phenyl Dibenzimidazole Tetrasulfonate | 3 | | | | | | | | | | |
| Neo Heliopan ® AP, 15% sol., neutralized with Biotive ® L-Arginine | Aqua, Disodium Phenyl Dibenzimidazole Tetrasulfonate, Arginin | | 6.7 | 6.7 | | | | | | | | |
| Neo Heliopan ® E 1000 | Isoamyl p.Methoxycinnamate | | 1 | | | | | | | | | |
| Neo Heliopan ® HMS | Homosalate | | 5 | | 5 | | | | | | | |
| Neo Heliopan ® Hydro, 20% sol., neutralized with Biotive ® L-Arginine | Aqua, Phenylbenzimidazole Sulphonic Acid, Arginin | | 10 | 10 | 10 | | | | | | | |
| Neo Heliopan ® MBC | 4-Methylbenzylidene Camphor | 1 | | | | | | | | | | |
| Neo Heliopan ® OS | Ethylhexyl Salicylate | | | 3 | 5 | | | | | | | |
| Neutral Oil | Caprylic/Capric Triglyceride | | | | | | 6 | | | | 13.7 | |
| Nicotinamide | Niacinamide | | | | | 0.5 | | | | | 1 | |
| Ozokerite Wax 2389 | Ozokerite | | | | | | | 2 | | | | |
| PCL-liquid 100 | Cetearyl Ethylhexanoate | | | 2 | | 4 | 5 | | | | | |
| PCL-Solid | Stearyl Heptanoate, Stearyl Caprylate | | | | | 3 | | | | 0.5 | | |
| Phytoconcentrole ® Coconut | Caprylic/Capric Triglyceride, Coconut (Cococ Nucifera) Oil | | | | | | | | 1 | | | |
| Rewoderm LI S80 | PEG-200 Hydrogenated Palmitate, PEG-7 Glyceryl Cocoate | | | | | | | | | 0.25 | | |
| Rewopol SBFA30 | Disodium Laureth Sulfosuccinate | | | | | | | | | 8 | | |
| Silcare Silicone 41M65 | Stearyl Dimethicone | | | 1 | | | | | | 21 | | |
| Sodium Chloride | Sodium Chloride | | | | | | | | | 1.7 | | |
| Sodium Hydroxide 10% sol. | Sodium Hydroxide | | | | | | 0.9 | | | | | |
| Solubilizer | PEG-40 Hydrogenated Castor Oil, Trideceth-9, | | | | | | | | 1.5 | | | 0.5 |

TABLE 9-continued

Air pollution protecting compositions

| Ingredients | INCI-Name | 7 | 8 | 9 | 10 | 11 | 12 | 13 | 14 | 15 | 16 | 17 |
|---|---|---|---|---|---|---|---|---|---|---|---|---|
| Sym3D ® | Propylene Glycol, Water (Aqua) Hydroxymethoxy phenyl Propylmethylmethoxybenzofuran | | | 0.2 | | | | | | | | |
| SymCalmin ® | Pentylene Glycol, Butylene Glycol, Hydroxyphenyl Propamido- benzoic Acid | | | | | 1 | | | | | | |
| SymClariol ® | Decylene Glycol | | | 0.5 | | | | | | | | |
| SymDecanox HA | Caprylic/Capric Triglyceride, Hydroxymethoxy phenyl Decanone | | | | | | | 1 | | | | |
| SymDiol ® 68 | 1,2 Hexanediol, Caprylyl Glycol | 0.6 | 0.5 | | | 0.5 | 0.8 | 0.5 | | | | 0.5 |
| SymFit ® 1617 | Trimethylcyclohexyl Butylcarbamate | | | | | | 0.1 | | | | | |
| SymFit ® nat 1750 | Propanediol, *Bobgunnia Madagascariensis* Wood Extract | | | | 1 | | | | | | | |
| SymGlucan ® | Water (Aqua) Glycerin, Beta Glucan | | 2 | | 2 | 1 | | 5 | | | | |
| SymMatrix ® | Maltodextrin, *Rubus Fruticosus* (Blackberry) Leaf Extract | | | | | | 0.5 | | | | | |
| SymMollient ® L | Neopentyl Glycol Diisononanoate | | | | | 2 | | | | | 5 | |
| SymMollient ® S | Cetearyl Nonanoate | | | | | 1 | | | | | 4 | |
| SymMollient ® W/S | Trideceth-9, PEG-5 Isononanoate | | | | | | | 2 | | | | |
| SymOcide ® PS | Phenoxyethanol, Decylene Glycol, 1,2-Hexanediol | | | | | 0.8 | | | | | | |
| SymRelief ® 100 | Bisabolol, *Zingiber Officinale* (Ginger) Root Extract | | | | | | | | 0.1 | | | |
| SymRelief ® S | Bisabolol, Hydroxymethoxy phenyl Decanone | | 0.1 | | | 0.2 | | | | | | |
| SymRepair ® | Hexyldecanol, Bisabolol, Cetylhydroxyproline Palmitamide, Stearic Acid, *Brassica Campestris* | | | 1 | | | 3 | | | | | |
| SymSave ® H | Hydroxyacetophenone | 0.5 | 0.8 | | 0.8 | | 0.8 | 0.5 | | 1.0 | | 0.5 |
| SymSitive ® 1609 | Pentylene Glycol, 4-t-Butylcyclo- hexanol | | | | | 0.5 | | | | | | |
| SymTriol ® | Caprylyl Glycol, 1,2-Hexanediol, Methylbenzyl Alcohol | | | 0.8 | | | | | | | | |
| SymVital ® | *Aloe Barbadensis* Leaf Juice Powder, Magnesium Ascorbyl Phosphate, *Rubus Idaeus* | 0.5 | | | | | | | | | | |
| SymWhite 377 (Symrise) | Phenylethyl resorcinol | | | 0.5 | | | | | 0.1 | | | |
| Tinosorb S | Bis-Ethylhexyl-oxyphenol, Methoxyphenyl Triazine | | | | | | | | | | 3 | |

TABLE 9-continued

Air pollution protecting compositions

| Ingredients | INCI-Name | 7 | 8 | 9 | 10 | 11 | 12 | 13 | 14 | 15 | 16 | 17 |
|---|---|---|---|---|---|---|---|---|---|---|---|---|
| Tapioca Pure | Tapioca Starch | | 5 | | | | | | | | | |
| TeCe-Ozokerit N502 | Ozokerite | | | | | | | | | | ad 100 | |
| Tego Betain L7 | Cocoamidopropyl Betaine | | | | | | | | | 5 | | |
| Tegosoft TN | C12-15 Alkyl Benzoate | | | | 5 | | | | | | | |
| Texapon N70 | Sodium Laureth Sulfate | | | | | | | | | 15 | | |
| Triethanolamine 99% | Triethanolamine | | | | | | | | | | | 0.5 |
| 3,3,5-Trimethylcyclohexyl Succinate Dimethylamide | 3,3,5-Trimethylcyclohexyl Succinate Dimethylamide | | | 0.5 | | | | | | | | |
| Vitamin E acetat | Tocopherol Acetate | | 0.5 | 0.5 | 0.5 | | 0.2 | | 0.5 | | 0.7 | |
| Wacker-Belsil CDM3526 VP | C26-C28 Alkyl Dimethicone | | | | | | | | | | 2 | |
| Water, demin. | Water (Aqua) | | | | | | Ad 100 | | | | | |

The invention claimed is:

1. A cosmetic composition, comprising
a mixture of purple coneflower pressed juice and ginger root CO2 extract, in a working amount of from about 0.01% by weight to about 2.5% by weight calculated on the final composition,
a cosmetically acceptable carrier selected from the group consisting of glycerol, 1,2-propylene glycol, 1,2-butylene glycol, 1,3-propylene glycol, 1,3-butylene glycol, ethanol, and mixtures thereof, and
at least one preservative,
wherein the ginger root CO2 extract contains
(a) 25 to 30% b.w. 6-gingerol,
(b) 5 to 10% b.w. 8-gingerol,
(c) 5 to 10% b.w. 10-gingerol,
(d) 1.5 to 4% b.w. 6-shogaol,
(e) 0.3 to 1.3% b.w. 8-shogaol,
(f) 0.03 to 1% b.w. 10-shogaol, and
(g) 0.01 to 1% b.w. zingerone,
on condition the amount of gingerols sums up to 35 to 50% b.w. and the amount of shogaols sums up to 1.5 to 6% b.w.

2. The composition of claim 1, which is a personal care composition, a skin care composition, a hair care composition or a sun care composition.

3. The composition of claim 1, which is a lotion, a cream, an emulsion, a foam, a mousse, an oil or a stick.

4. The composition of claim 1, wherein said mixture of purple coneflower pressed juice and ginger root CO2 extract is present in an amount of from about 0.05% by weight to about 1.0% by weight—calculated on the final composition.

5. The composition of claim 1, wherein said at least one preservative is selected from the group consisting of phenoxyethanol, formaldehyde solution, parabens, pentanediol, sorbic acid, hydroxy acetophenone, and mixtures thereof.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Bacillus megaterium

<400> SEQUENCE: 1
gccgctagag gtgaaattct tg                                              22

<210> SEQ ID NO 2
<211> LENGTH: 21
<212> TYPE: DNA
<213> ORGANISM: Bacillus megaterium

<400> SEQUENCE: 2
cattcttggc aaatgctttc g                                               21

<210> SEQ ID NO 3
<211> LENGTH: 24
<212> TYPE: DNA
<213> ORGANISM: Bacillus megaterium

<400> SEQUENCE: 3
agatggtcaa ggagcactac aaaa                                            24

<210> SEQ ID NO 4
<211> LENGTH: 22
<212> TYPE: DNA
<213> ORGANISM: Bacillus megaterium

<400> SEQUENCE: 4
gctcaatcag gctgtctgtg at                                              22

<210> SEQ ID NO 5
<211> LENGTH: 20
<212> TYPE: DNA
<213> ORGANISM: Bacillus megaterium

<400> SEQUENCE: 5

-continued

```
cctcgagccc accgggaacg                                              20

<210> SEQ ID NO 6
<211> LENGTH: 22
<212> TYPE: DNA
<213> ORGANISM: Bacillus megaterium

<400> SEQUENCE: 6
aactggaccg aaggcgcttg tg                                           22

<210> SEQ ID NO 7
<211> LENGTH: 18
<212> TYPE: DNA
<213> ORGANISM: Bacillus megaterium

<400> SEQUENCE: 7
tggaagtgcg tggctggt                                                18

<210> SEQ ID NO 8
<211> LENGTH: 19
<212> TYPE: DNA
<213> ORGANISM: Bacillus megaterium

<400> SEQUENCE: 8
tgcactccag caggttgct                                               19

<210> SEQ ID NO 9
<211> LENGTH: 21
<212> TYPE: DNA
<213> ORGANISM: Bacillus megaterium

<400> SEQUENCE: 9
tgaaaggtgg accaacaatt t                                            21

<210> SEQ ID NO 10
<211> LENGTH: 20
<212> TYPE: DNA
<213> ORGANISM: Bacillus megaterium

<400> SEQUENCE: 10
ccaagagaat ggccgagttc                                              20
```